United States Patent [19]

Horiguchi et al.

[11] 4,171,987

[45] Oct. 23, 1979

[54] MICRO-POROUS SHEET

[75] Inventors: Masaru Horiguchi; Nobuo Hiratsuka; Sumio Otani, all of Minami-ashigara, Japan

[73] Assignee: Fuji Photo Film Co., Ltd., Minami-ashigara, Japan

[21] Appl. No.: 558,099

[22] Filed: Mar. 13, 1975

[30] Foreign Application Priority Data

Mar. 13, 1974 [JP] Japan .................................. 49-28845

[51] Int. Cl.$^2$ .............................................. C08L 1/12
[52] U.S. Cl. .................... 106/122; 106/195; 106/196; 106/197 R; 264/49
[58] Field of Search ..................... 166/122; 264/44, 41

[56] References Cited

U.S. PATENT DOCUMENTS

| | | | |
|---|---|---|---|
| 3,428,584 | 2/1969 | Riley | 264/41 X |
| 3,892,665 | 7/1975 | Steigelman | 210/500 M |

OTHER PUBLICATIONS

Research & Development Progress, Rpt. #177–Fabrication & Evaluation of New Ultrathin Reverse Osmosis Membranes, pp. 38–41, Feb. 1969.
Chem Abst. 64: 17.822q.
Riley, R. L. et al., "Improved Reverse Osmosis Membranes," U.S. Dept. of Interior, Office of Saline Water, Research and Development Progress Report No. 729, Dec. 1971.

*Primary Examiner*—Theodore Morris
*Attorney, Agent, or Firm*—Sughrue, Rothwell, Mion, Zinn and Macpeak

[57] ABSTRACT

A micro-porous sheet having excellent thermostability which contains a cellulose ester as a basic component and 0.1 to 20 wt% of a cellulose ether based on the cellulose ester.

6 Claims, No Drawings

MICRO-POROUS SHEET

BACKGROUND OF THE INVENTION

1. Field of the Invention

This invention relates to a micro-porous sheet and, in particular, to a micro-porous sheet having improved stability at high temperatures.

2. Description of the Prior Art

Micro-porous sheets have long been known (for example, refer to R. Kesting *Synthetic Polymer Membranes,* McGraw-Hill (1971)) and are used widely, for example, as a filter.

Micro-porous sheets have heretofore been produced starting from cellulose esters as described, for example, in U.S. Pat. Nos. 1,421,341, 3,133,132 and 2,944,017 and Japanese Pat. Publication Nos. 15,698/68, 33,313/70, 39,586/73 and 40,050/73. However, the micro-porous sheets produced from cellulose esters have limited applications because they are very unstable at high temperatures. For example, micro-porous sheets containing cellulose acetate as a basic component and used for the filtration of pharmaceuticals have a disadvantage in that the filtration capacity of the sheets is markedly reduced, because of the hydrolysis of the cellulose acetate, through heating with steam under pressure or the like, which conditions are usually employed in the sterilization of the sheet before use. Therefore, only specific and restricted methods such as gas sterilization can be employed for the sterilization of the micro-porous sheets containing cellulose acetate as a basic component, so that the applications of such mirco-porous sheets have been limited markedly in the pharmaceutical industry.

SUMMARY OF THE INVENTION

An object of this invention is to overcome the above defect of the micro-porous sheets of the prior art.

A further object of this invention is to provide a micro-porous sheet with excellent thermostability.

Another object of this invention is to provide a process for producing a micro-porous sheet with excellent thermostability.

Various approaches have been studied and, as a result, it has now been found that the above objects of this invention can be accomplished with a micro-porous sheet from a cellulose ester as a basic component containing about 0.1 to 20 wt% of a cellulose ether based on the cellulose ester.

DETAILED DESCRIPTION OF THE INVENTION

Cellulose esters are used in this invention as a basic component in the formation of the micro-porous sheet. The term "basic component" as used herein means that the component is a basic film-forming component as well as a basic component of a micro-porous sheet. Suitable cellulose esters which can be used in this invention are those having a degree of polymerization of about 100 to 500, preferably 120 to 380, and include cellulose diacetate, cellulose triacetate, nitrocellulose, cellulose acetate butyrate, cellulose propionate and mixtures of these cellulose esters. In particular, cellulose diacetate, cellulose triacetate, cellulose acetate butyrate and mixtures of two or more of these cellulose esters are especially useful. Above all, those cellulose esters containing about 30 wt% or more, particularly 60 wt% or more, of a cellulose organic acid ester are even more preferred. A suitable degree of esterification is such that the proportion of the three OH groups per glucose unit of cellulose remaining unesterified is about 0.05 to 1.35 and for cellulose acetate preferably 0.05 to 0.75, for nitrocellulose preferably 0.60 to 1.30 and for cellulose acetate butyrate preferably 0.08 to 0.55. A suitable butyrate:acetate weight ratio ($C_3H_7CO/CH_3CO$) in cellulose acetate butyrate can range from about 0.55:1 to 9.0:1.

Thus far, in the production of micro-porous sheets, a phase separation of the cellulose ester from a solution containing the cellulose ester has usually been employed. This procedure is also preferably used in this invention. That is, a micro-porous sheet is obtained by preparing a cellulose ester solution containing a good solvent and a poor solvent and/or a non-solvent for the cellulose ester, coating or casting the solution of the cellulose ester on a support and then drying the coating or casting to form a film of the cellulose ester and finally peeling off the film from the support.

The term "good solvent" as used herein designates those solvents or mixtures of solvents which dissolve the cellulose ester, preferably to an extent of not less than about 5% by weight of the cellulose ester, and are more volatile than the poor solvent and the non-solvent or boil at lower temperatures, particularly about 15° C. or lower. Although it is rather difficult to unequivocally define good solvents generally used for cellulose esters since the choice of solvent depends upon the ester residue of the cellulose ester used, one or more good solvents can be selected, for example, from halogenated hydrocarbons such as methylene chloride, chloroform, ethylene chloride, ethylidene chloride, trichloroethane, tetrachloroethane or ethyl bromide, ketones such as acetone, methyl ethyl ketone, methyl isobutyl ketone or cyclohexanone, ethers such as dioxane, tetrahydrofuran, methyl cellosolve or ethyl cellosolve, esters such as methyl formate, ethyl formate, propyl formate, butyl formate, methyl acetate, ethyl acetate, propyl acetate, butyl acetate, amyl acetate, methyl propionate, ethyl propionate, methyl butyrate or ethyl butyrate, aliphatic acids such as formic acid, acetic acid or propionic acid, and nitrogen-containing compounds such as nitromethane, nitroethane, nitropropane, dimethylformamide or morpholine. Good solvents boiling at below about 80° C. are particularly preferred from the standpoint of ease of handling.

The term "poor solvent" as used herein designates a single solvent or a mixture of solvents which is not capable of dissolving the cellulose ester or which dissolves the cellulose ester to an extent of less than about 5% by weight of the cellulose ester. The poor solvent preferably is capable of not dissolving the cellulose ester but only swelling the cellulose ester wherein the degree of swelling (swelled cellulose ester/non-swelled ester) is preferably greater than about 1.5. Poor solvents, thus, are those which do not substantially dissolve and only swell the cellulose ester and desirably are miscible with the good solvent. Although it is difficult to specifically define the poor solvents since their choice also depends upon the ester residue of the cellulose ester used, they are, for example, halogenated hydrocarbons such as ethylene chloride, ethylidene chloride, trichloroethane, tetrachloroethane, carbon tetrachloride, trichloroethylene, amyl chloride, butyl chloride, ethylene bromide or chlorobenzene, aliphatic alcohols and alicylic alcohols such as methanol, ethanol, propanol, butanol, amyl alcohol, diacetone alcohol, hexanol or cyclohexanol, ethers such as isopropyl ether, dibutyl ether, tetrahydrofuran or tetrahydropyran, ketones such as acetone, methyl ethyl ketone, methyl isobutyl ketone, diethyl ketone, diisobutyl ketone or acetophenone, esters such as butyl formate, amyl formate, ethyl acetate, propyl acetate, butyl acetate, isoamyl acetate, ethyl propionate, ethyl benzoate, propyl benzoate, methyl salicylate or diethyl oxalate, and aliphatic acids such as formic acid, acetic acid, propionic acid, butyric acid or lactic acid. One or more of these poor solvents can be selected. Particularly preferred are those poor solvents which are less volatile or have a higher boiling point than the good solvent.

The term "non-solvent" as used herein designates a solvent which does not dissolve the cellulose ester and further wherein the degree of swelling is less than about 1.5. Thus, non-solvents are those solvents which do not substantially dissolve nor swell the cellulose ester and are miscible with the poor solvent. As the non-solvent, water is used in most cases, and sometimes aliphatic hydrocarbons such as hexane, heptane or decane, alicyclic hydrocarbons such as cyclohexane, aromatic hydrocarbons such as toluene, benzene or tetralin, alcohols such as ethylene glycol, ethylene glycol monomethyl ether, ethylene glycol monoethyl ether or diethylene glycol, or the like, can be used.

Each of the above three types of solvents can be, of course, used in admixture respectively.

The term "good solvent", "poor solvent" and "non-solvent" used in this invention are relative definitions determined mainly based upon their dissolving capability and swelling action on a cellulose ester. Therefore, these definitions can not be unequivocally applied to individual solvents since the action of each individual solvent will differ depending or the particular cellulose ester. The kinds of good solvent, poor solvent and non-solvent will therefore vary or may be even replaced with each other depending upon the kind of the ester residue of the cellulose ester used. However, this relationship is based upon the chemical and physical properties of the cellulose ester, and the cellulose ester and the three types of the solvents can be readily selected by those skilled in the art based on common knowledge. Similar usages of these terms appear in R. Kesting, *Synthetic Polymer Membranes*, Chapter V, McGraw-Hill (1971).

There are no particular restrictions on the manner of dissolving and mixing the cellulose ester, the good solvent, the poor solvent and the non-solvent. Numerous techniques can be suitably used in the invention. Exemplary techniques include dissolving the cellulose ester in a good solvent and then adding a poor solvent and a non-solvent to the solution and dissolving the cellulose ester in a mixture of a good solvent and some portion of a poor solvent, adding the remaining poor solvent to the solution and then adding a non-solvent. In addition, no special restrictions are imposed on conditions such as the mixing ratio of solvents and the temperature of mixing (although it is preferred to employ temperatures below the boiling point of the solvents). Moreover, in some cases, neither a poor solvent nor a non-solvent is used. That is, a good solvent can be combined with a poor solvent or a non-solvent by using an inorganic salt or the like. Dissolving and mixing are desirably carried out so as to produce a stable solution, since a stable cellulose ester solution facilitates the subsequent operations. A stable solution is a solution in which no gelation of the cellulose ester nor phase separation occurs. A stable solution can be prepared, for example, using a good solvent in a larger amount than the amount of the other solvents used, or adding and dissolving the cellulose ester in a mixture of all of the good solvent and some of the poor solvent.

An important feature of this invention is a micro-porous sheet comprising a cellulose ester having a cellulose ether contained therein. There are no particular restrictions on the addition of the cellulose ether. For example, the cellulose ether can be added to a cellulose ester solution in the presence of water. However, it is advantageous to add the cellulose ether in an amount of about 0.1 to about 20.0 wt%, preferably 0.5 to 5 wt%, based on the cellulose ester used. If the cellulose ether is added in an amount more than about 20 wt%, the system becomes somewhat non-uniform, resulting in uneven size distribution of micro-pores finally formed. On the other hand, with an amount less than about 0.1 wt%, the objects of this invention can not be attained.

Suitable cellulose ethers used in the invention include those having hydroxyl groups, some of which are etherified, for example, methyl cellulose and ethyl cellulose. Methyl cellulose and ethyl cellulose preferably have an average molecular weight of about 20,000 to about 200,000, particularly 30,000 to 50,000. A methyl cellulose and ethyl cellulose which have an average substitution degree of about 1.0 to 1.9 are particularly advantageous. The term "substitution degree" as used herein refers to the number of hydroxyl groups, which are substituted with a substituent, in one unit of cellulose having three hydroxyl groups. For example, when one hydroxyl group is substituted with e.g., a methoxy group, the substitution degree is 1. The "cellulose ether" used in this invention have the structure shown below.

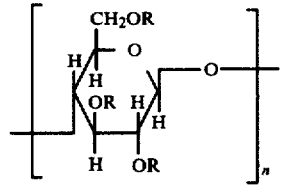

wherein n represents the degree of polymerization and R represents —H, —CH$_3$, or —CH$_2$CH$_3$, with the average degree of substitution where R is —CH$_3$ or —CH$_2$CH$_3$ ranging from about 1.0 to 1.9 and where a portion of the —CH$_3$ and —CH$_2$CH$_3$ groups can be replaced by a member selected from the group consisting of —CH$_2$CH$_2$OH, —CH$_2$CH$_2$CH$_2$OH, —CH$_2$C-H$_2$OOCCH$_3$, —CH$_2$CH$_2$CH$_2$OOCCH$_3$,

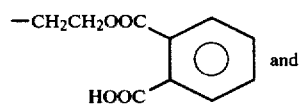

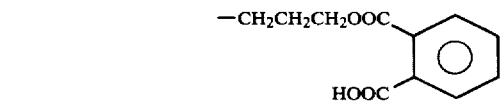

such that the average degree of substitution by the —CH$_2$CH$_2$OH, —CH$_2$CH$_2$CH$_2$OH, —CH$_2$C-H$_2$OOCCH$_3$,

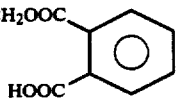
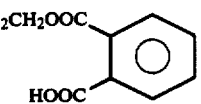

groups ranges from 0 to about 0.3. Where R is H, the hydroxyl position is unsubstituted. As described above, the specific cellulose ethers which can be used in this invention also include those (with a substitution degree of about 0.1 to 0.3) having as a substituent one or more of a hydroxyalkoxy group such as a hydroxyethoxy group or a hydroxypropoxy group, or a reaction product of the hydroxyalkoxy group with, e.g., phthalic anhydride, acetic anhydride, acetic chloride, or the like. Suitable specific examples are hydroxyethyl cellulose, hydroxypropyl methyl cellulose, hydroxypropyl ethyl cellulose, acetylpropyl methyl cellulose, carboxy-benzoyloxypropyl methyl cellulose, carboxy-benzoyloxypropyl ethyl cellulose, etc. Preferred cellulose ethers include methylcellulose, ethylcellulose, hydroxypropyl methyl cellulose, and carboxybenzoyloxypropyl methyl cellulose.

In the preparation of the micro-porous sheet of this invention, a plasticizer such as organic phosphoric esters, phthalic esters or glycerol esters; a moisture absorbent such as glycerol or a diglyceride; an anionic surface active agent such as a higher carboxylic acid salt, a salt of a higher alcohol sulfate, a salt of a polyethylene glycol ether sulfate, a salt of a alkylarylsulfonate or a salt of a phosphate; a cationic surface active agent such as an amine salt or an ammonium salt; and amphoteric surface active agent such as dodecylaminoethylglycine hydrochloride; and a nonionic surface active agent such as an alkyl ether, an alkyl aryl ether, a sorbitan monoalkyl ester, a polyoxyethylene alkylamine, a polyoxyethylene alkylamide, a polyethyleneimine, a polyeoxyethylene, a polyoxypropylene, a glycol ester, a sucrose ester, an aliphatic ethanolamide, a methylolamide or a glycoside can be also used. As a surface active agent, it is particularly advantageous to use nonionic surface active agents which can be added to food, e.g., stearic acid monoglyceride, a polyoxyethylene sorbitan monostearate, a polyoxyethylene octylphenol ether or a propylene glycol monooleate. Moreover, various additives such as a micropore-forming aid, i.e., an inorganic salt, e.g., calcium chloride, sodium chloride, magnesium chloride, sodium sulfate, etc. and a pore size modifier such as starch can be added. It is apparent to those skilled in the art that the amounts of the additives used can be varied widely depending upon the purpose. Specific examples and amounts of the additives which can be used are described in detail in U.S. Pat. No. 3,547,809 and Japanese Patent Publication No. 40,050/73. In addition, the above described cellulose ether tends to act also as a moisture absorbent and a surface active agent.

The cellulose ester solution thus prepared is coated or cast on a support such as glass, film or cloth. The film on the support is dried simultaneously with or after the coating or casting. Drying is carried out for the purpose of causing a phase separation of the cellulose ester in the film and is usually conducted at temperatures below the boiling point of the good solvent, preferably at temperatures at which the cellulose ester easily gels (i.e., about $-150°$ C. to $35°$ C.). In this case, a prolonged drying time (i.e., slow drying) renders the size of the micropores uniform, while a shorter drying time (i.e., rapid drying) results in an uneven size. Drying causes a coacervation in the film, and then the cellulose ester gells. The film on the support can be sufficiently dried by heating usually at temperatures below the softening point of the cellulose ester after the formation of micropores. Various methods for the production of a microporous filter are already well-known and described, for example, in the above-described prior patent specifications and U.S. Pat. Nos. 3,129,159 and 3,428,584. After adequately applying such methods, the film is peeled off from the support to provide a micro-porous sheet having an average pore size less than about $10\mu$, particularly ranging from 0.05 to $5\mu$.

The micro-porous sheet obtained by the process of this invention does not undergo hydrolysis and exhibits a very good filtering action even when exposed at high temperatures of about $125°$ C., so that it can withstand any type of treatments without a reduction in the filtration capacity. Therefore, there are no restrictions on the applications of the micro-porous sheet of this invention.

The micro-porous sheet obtained by the process of this invention is applicable not only as a filter for filtering bacteria but also as a filter for filtering proteins, viruses, etc., a filter for the reverse osmosis process used for converting sea water into fresh water and as an electrophoresis membrane.

This invention is explained in greater detail by reference to the following examples. All parts, percents, ratios and the like used in the following examples are by weight unless otherwise indicated.

EXAMPLE 1

A solution having the following composition was prepared.

|  | Parts |
| --- | --- |
| Cellulose Triacetate* | 4 |
| Cellulose Diacetate** | 2 |
| Methyl Cellulose*** | 0.05 |
| Methylene Chloride | 54 |
| Methanol | 35 |
| Water | 5 |

*Average degree of polymerization: 370; Esterification degree: 43.4%
**Average degree of polymerization: 150; Esterification degree: 39.6%
***Molecular weight: about 40,000; Substitution: 1.85

The above solution was cast in a thickness of about 1 mm on a plate. Drying was effected at room temperature (i.e., $20°–30°$ C.) for the first 30 minutes. Thereafter, the film was peeled off from the plate and dried at room temperature for 2 hours and subsequently at about $80°$ C. for 1 hour. The Micro-Porous Sheet A thus formed had a thickness of $130\mu$, a void content of 79% and a bubble point (as measured according to ASTM-F-316-70) of 2.85 kg/cm$^2$. On the other hand, Micro-Porous Sheet B, a conventional sheet, was prepared in quite the same manner as described above from a solution of the above composition except that methyl cellulose was not employed. Micro-Porous Sheet B had a void content of 80% and a bubble point of 2.80 kg/cm$^2$. Micro-Porous Sheets A and B were respectively subjected to a compressed steam treatment at $121°$ C. for 20 minutes and then the amount of distilled water filtered through the sheet was determined.

The results obtained are shown in the following.

|  | Micro-Porous Sheet | |
| --- | --- | --- |
|  | Sheet A (ml/cm²/min) | Sheet B (ml/cm²/min) |
| Untreated | 55 | 58 |
| Treated with Compressed Steam | 55 | 37 |

As is apparent from the above results, the filtration capacity of the conventional Mirco-Porous Sheet B was reduced to 64% after the compressed steam treatment, while Mirco-Porous Sheet A of this invention showed no reduction at all in the filtration capacity.

EXAMPLE 2

A solution having the following composition was prepared.

|  | Parts |
| --- | --- |
| Cellulose Triacetate* | 2 |
| Cellulose Diacetate** | 4 |
| Ethyl Cellulose*** | 0.10 |
| Methylene Chloride | 55 |
| Ethanol | 34 |
| Water | 5 |

*Average degree of polymerization: 240; Esterification degree: 44.0%
**Average degree of polymerization: 150; Esterification degree: 39.6%
***Average molecular weight: 80,000; Substitution degree: 1.80

A micro-porous sheet was prepared in the same manner as in Example 1 using the above solution. The sheet had a thickness of 140μ, a void content of 81% and a bubble point of 2.75 kg/cm². The amount of distilled water filtered through the sheet was determined before and after the compressed steam treatment in the same manner as in Example 1. The results obtained are shown in the following table.

Untreated—61 ml/cm²/min
Treated with compressed steam—61 ml/cm²/min

As is apparent from the above results, the combined use of the cellulose ester and the cellulose ether improves the heat-resistance remarkably.

While the invention has been described in detail and with reference to specific embodiments thereof, it will be apparent to those skilled in the art that various changes and modifications can be made therein without departing from the spirit and scope thereof.

We claim:

1. A micro-porous sheet comprising a cellulose ester as a basic component and about 0.1 to 20 wt% of a cellulose ether based on the cellulose ester wherein said cellulose ester is cellulose diacetate, cellulose triacetate, nitrocellulose, cellulose acetate butyrate, cellulose propionate or a mixture thereof and said cellulose ether has the formula

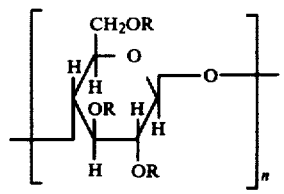

wherein n is the degree of polymerization, and R is —H, —CH₃, or —CH₂CH₃, with the average degree of substitution where R is —CH₃ or —CH₂CH₃ ranging from about 1.0 to 1.9 and where a portion of the —CH₃ and —CH₂CH₃ groups can be replaced by a member selected from the group consisting of —CH₂CH₂OH, —CH₂CH₂CH₂OH, —CH₂CH₂OOCCH₃, —CH₂CH₂CH₂OOCCH₃,

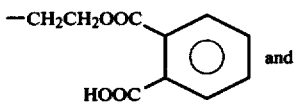
and
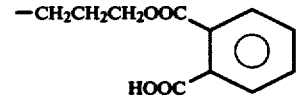

such that the average degree of substitution by said member ranges from 0 to about 0.3 and wherein the average pore size of the microporous sheet is less than 10 microns.

2. The micro-porous sheet of claim 1 wherein the average pore size of the pores of said micro-porous sheet is from 0.05 to 5 microns.

3. The micro-porous sheet of claim 1, wherein said cellulose ester contains about 30 wt% or more of a cellulose organic acid ester.

4. The micro-porous sheet of claim 1, wherein said cellulose ether is methyl cellulose, ethyl cellulose, hydroxyethyl cellulose, hydroxypropyl methyl cellulose, hydroxypropyl ethyl cellulose, acetylpropyl methyl cellulose, carboxy-benzoyloxypropyl methyl cellulose, or carboxy-benzoyloxypropyl ethyl cellulose or a mixture thereof.

5. The micro-porous sheet of claim 1, wherein said cellulose ether has an average molecular weight of about 20,000 to about 200,000.

6. The micro-porous sheet of claim 4, wherein said cellulose ether is methylcellulose, ethylcellulose, hydroxypropyl methyl cellulose, or carboxybenzoyloxypropyl methyl cellulose.

* * * * *